(12) United States Patent
D'Arrigo et al.

(10) Patent No.: US 9,655,972 B2
(45) Date of Patent: May 23, 2017

(54) METHOD FOR THE TREATMENT OF NANOHYDROGELS

(71) Applicant: NIOB SAGL, Lugano (CH)

(72) Inventors: Giorgia D'Arrigo, Monte Argentario (IT); Claudia Cencetti, Rome (IT); Chiara Di Meo, Bucchianico (IT); Pietro Matricardi, Rome (IT)

(73) Assignee: NIOB sagl, Lugano (CH)

( * ) Notice: Subject to any disclaimer, the term of this patent is extended or adjusted under 35 U.S.C. 154(b) by 0 days.

(21) Appl. No.: 14/896,974

(22) PCT Filed: Jun. 11, 2014

(86) PCT No.: PCT/IB2014/062139
§ 371 (c)(1),
(2) Date: Dec. 9, 2015

(87) PCT Pub. No.: WO2014/199319
PCT Pub. Date: Dec. 18, 2014

(65) Prior Publication Data
US 2016/0151500 A1 Jun. 2, 2016

(30) Foreign Application Priority Data

Jun. 11, 2013 (IT) .............. RM2013A0340

(51) Int. Cl.
| | |
|---|---|
| C08J 3/075 | (2006.01) |
| A61K 47/36 | (2006.01) |
| A61L 2/04 | (2006.01) |
| A61K 47/26 | (2006.01) |
| A61K 9/10 | (2006.01) |
| A61K 9/19 | (2006.01) |
| A61K 9/51 | (2006.01) |
| A61L 2/00 | (2006.01) |
| A61L 2/07 | (2006.01) |
| A61K 31/5383 | (2006.01) |
| A61K 47/28 | (2006.01) |

(52) U.S. Cl.
CPC .............. *A61K 47/36* (2013.01); *A61K 9/10* (2013.01); *A61K 9/19* (2013.01); *A61K 9/5123* (2013.01); *A61K 9/5161* (2013.01); *A61K 9/5192* (2013.01); *A61K 31/5383* (2013.01); *A61K 47/26* (2013.01); *A61K 47/28* (2013.01); *A61L 2/0023* (2013.01); *A61L 2/04* (2013.01); *A61L 2/07* (2013.01); *C08J 3/075* (2013.01); *C08G 2210/00* (2013.01); *C08J 2305/00* (2013.01); *C08J 2305/08* (2013.01)

(58) Field of Classification Search
CPC .................. C08J 3/075; A61K 47/36
See application file for complete search history.

(56) References Cited

FOREIGN PATENT DOCUMENTS

| | | |
|---|---|---|
| EP | 1 666 075 A1 | 6/2006 |
| JP | 2007-68696 A | 3/2007 |

OTHER PUBLICATIONS

I. Lee, et al., "Single molecular mechanics of a cholesterol-bearing pullulan nanogel at the hydrophobic interfaces", Biomaterials, Elsevier Science Publishers BV., Barking, GB, vol. 25, No. 15, Jul. 1, 2004, pp. 2911-2918.
G. D'Arrigo, et al. "Self-assembled gellan-based nanohydrogels as a tool for prednisolone delivery", Soft Matter, vol. 8 No. 45, Jan. 1, 2012, pp. 11557-11564.
K. Akiyoshi, et al. "Microscopic Structure and Thermoresponsiveness of a Hydrogel Nanoparticle by Self-Assembly of a Hydrophobized Polysaccharide", Macromolecules, American Chemical Society, US, vol. 30, No. 4, Jan. 1, 1997, pp. 857-861.

*Primary Examiner* — Carlos Azpuru
(74) *Attorney, Agent, or Firm* — Blank Rome LLP

(57) ABSTRACT

A method for treating nanohydrogels comprising—a dispersion step, in which a nanohydrogel obtained from a polysaccharide functionalized with hydrophobic molecules is dispersed in an aqueous solution, and a sterilization and homogenization step, in which the aqueous dispersion of nanohydrogels is added with a compound designed to be charged in the nanohydrogel particles by being englobed or adsorbed thereby and is subjected to a temperature of between 70° C. and 150° C. and a pressure of between 1 and 5 bar; in said sterilization and homogenization step, the conditions of temperature and pressure must be such that boiling of the aqueous dispersion of nanohydrogels does not occur.

7 Claims, No Drawings

METHOD FOR THE TREATMENT OF NANOHYDROGELS

TECHNICAL FIELD

The present invention relates to a method for treating nanohydrogels.

By the term "nanohydrogels" is meant a particular type of nanoparticles with a size of between 10 nm and 1000 nm that is able to combine the advantages of hydrogels with those of nanotechnology, such as for example high flexibility, versatility, water absorption, high biocompatibility, and long stay times within the organism.

BACKGROUND ART

In general, it is known that a polysaccharide (of a hydrophilic nature) appropriately functionalized with molecules of a hydrophobic nature can provide an assembling system with nanohydrogel characteristics if it is exposed in particular conditions to an aqueous environment.

Currently known are various methods for preparing nanohydrogels starting from functionalized polysaccharides.

A first of these methods consists in subjecting the functionalized polysaccharide to sonication. Ultrasonic vibrations are able to induce formation of nanohydrogels of small size. Ultrasounds generate in the polymeric dispersion micro-bubbles that by imploding give rise to the phenomenon of cavitation, which promotes separation of the polymeric chains, thus favouring formation of a dispersion of nanoparticles.

Another method consists in solubilizing the functionalized polysaccharide in an appropriate solvent and adding drop by drop the solution obtained in water. In these conditions, the system precipitates inducing formation of nanoparticles.

Yet another method consists in subjecting to dialysis against water or aqueous solution the functionalized polysaccharide once this has been solubilized in an organic solvent. Slow entry of water through the dialysis tubes causes formation of nanohydrogels of small size by spontaneous self-assembly.

Nanohydrogels are acquiring an increasing importance in the pharmaceutical field thanks to the fact that, if they are rendered sterile and apyrogenic, they can be used as compounds for vehicling drugs and be administered both in humans and in animals via inhalatory or parenteral route (i.v., i.m., s.c.,) or else topically, with the aid of an appropriate device.

Nanohydrogels, in fact, can englobe or adsorb a pharmacologically active principle and function as carrier for its administration.

In order to be used as drug carrier, the nanohydrogel must necessarily be subjected to a sterilization treatment. The sterilization methods used by pharmaceutical industries not are, however, totally satisfactory.

One of the main sterilization methods used is filtration by means of filters with a porosity equal to or less than 0.22 μm following the pharmacopoeia recommendations. Even though filtration is possible as a rule with systems of suitable dimensions, it is in any case frequently problematical on account of clogging of the filters themselves due to the interactions that may arise between the nanoparticles and the materials constituting the filters. Furthermore, it has been found that filtration causes, as a mechanical effect, destructuring of the nanoparticles, for example vesicles such as liposomes, causing the loss of the medicament of the bioactive molecules, which remain trapped on the filter, and/or their leakage into the transport liquids.

Another sterilization method consists in irradiation with gamma rays or with a electron flow. This procedure presents the disadvantage of being such as to alter the structure of the fragile bio-active molecules, cause a degradation of the polymers that constitute the pharmaceutical form, and alter the integrity of the system itself.

Another method used for sterilization envisages the use of gases, such as ethylene oxide; this technique, however, is not easy to implement in the presence of substances that can react with the gas itself. Furthermore, also the intimate contact with the pharmaceutical forms, necessary for achieving sterility, may prove problematical, as likewise removal of the gas prior to packaging of the pharmaceutical form itself.

A necessary characteristic to guarantee a correct and controllable use of nanohydrogels in biomedical and pharmaceutical applications regards the dimensional homogeneity of the nanohydrogels themselves. As is known, a high dimensional dishomogeneity may not enable a correct control of the efficacy of the nanohydrogels as drug carriers.

Furthermore, another requirement for a correct use of nanohydrogels as drug carriers is that of guaranteeing effective englobing or adsorption of the pharmacologically active compound in the nanohydrogels themselves.

Finally, there is required the possibility of being able to lyophillize nanohydrogels either by themselves or with the pharmacologically active compound so that they are more convenient to transport, preserve, and handle. At the moment when the nanohydrogels are to be used, they will then be reconstituted by simple addition of water or of a physiological solution. As may be immediately understandable to a person skilled in the sector, in order to be able to guarantee stability of, the nanohydrogels following upon the lyophilization treatment, it is necessary for them to be also effectively protected by suitable cryoprotectants by appropriate addition thereof to the nanohydrogels themselves.

There is hence felt the need to provide a methodology that will be able to provide in a simple and economically advantageous way an effective sterilization of the nanohydrogels and at the time same will be able to guarantee a high dimensional homogeneity of the nanohydrogels themselves.

Furthermore, there is also felt the need to provide a simple and economically advantageous method that will enable "charging" of the nanohydrogels with a pharmacologically active compound and/or with a cryoprotective compound.

The inventors of the present patent application have unexpectedly found a method for sterilization and charging of nanohydrogels that, at the same time, manages to provide a greater dimensional homogeneity as compared to the starting nanohydrogels.

DISCLOSURE OF INVENTION

The subject of the present invention is a method for treating nanohydrogels, characterized in that it comprises a dispersion step, in which a nanohydrogel obtained from a polysaccharide functionalized with hydrophobic molecules is dispersed in an aqueous solution to obtain an aqueous dispersion of nanohydrogels, and a sterilization and homogenization step, in which the aqueous dispersion of nanohydrogels is subjected to a temperature of between 70° C. and 150° C. and a pressure of between 1 bar and 5 bar; in said sterilization and homogenization step, the conditions of temperature and pressure must be such that boiling of the aqueous dispersion of nanohydrogels does not take place.

BEST MODE FOR CARRYING OUT THE INVENTION

Preferably, the sterilization and homogenization step envisages a temperature of between 90° C. and 130° C. and a pressure of between 1.5 bar and 3.5 bar.

Preferably, the sterilization and homogenization step has a duration of between 5 min and 3 h.

Preferably, the sterilization and homogenization step envisages that added to the aqueous dispersion of nanohydrogels is a compound designed to be charged in the nanohydrogel particles by being englobed or adsorbed thereby.

Preferably, the aforesaid compound designed to be englobed and/or adsorbed in the nanohydrogel particles is a cryoprotective compound and/or a pharmacologically active compound.

Preferably, said cryoprotective compound is added to the aqueous dispersion of nanohydrogels in a concentration of between 0.10% w/v and 20.0% w/v.

Preferably, said cryoprotective compound is comprised in the group made up of dextrose, maltose, trehalose, lactose, and saccharose.

Preferably, said pharmacologically active compound is added to the aqueous dispersion of nanohydrogels in a concentration of between 0.05 mg/ml and 10.0 mg/ml.

Preferably, the nanohydrogels are self-assembled nanohydrogels derived from polysaccharides functionalized with molecules having a hydrophobic nature.

Preferably, the polysaccharide is comprised in the group constituted by hyaluronic acid, pullulan, dextran, gellan gum, scleroglucan, chitosan, alginate, guaran, xanthan gum, chitosan, and cyclodextrin.

Preferably, said pharmacologically active compound is comprised in the group made up of antibiotics, anti-cancer agents, analgesics, anti-inflammatory agents, anaesthetics, analeptics, adrenergic agents, adrenergic blocking agents, anticholinergic agents, anticolinesterasic agents, anticonvulsivants, adrenocorticotropic agents, adrenolytic agents, adrenomimetic agents, alkylating agents, alkaloids, allosteric inhibitors, anabolic steroids, anorectics, antacids, antidotes, antidiarrhoeal agents, antifolates, antipyretics, antirheumatic agents, psychotherapeutic agents, neural blocking agents, antiemetics, anthelmintics, antiarrhythmic agents, antitubercular agents, anticoagulants, antidepressants, antidiabetic agents, antiepileptic agents, antifungal agents, histamine antagonists, antihypertensives, muscarinic antagonists, antimycobacterials, antimalarial agents, antiseptics, antiprotozoal agents, immunosuppressants, immunostimulants, antithyroid agents, antiviral agents, anxiolytics, sedatives, astringents, beta-blocking agents, contrast media, corticosteroids, anticough agents, diagnostic agents, image-diagnostic agents, diuretics, dopaminergic agents, haemostatic agents, haematological agents, haemoglobin modifiers, hormones, hypnotic agents, hypolipidemizing agents, lipid-regulating agents, muscarinic agents, parasympathicomimetic agents, myorelaxing agents, prostaglandins, sedatives, sexual hormones, anti-allergens, stimulating agents, sympathicomimetic agents, thyroid agents, vasodilators, vaccines, vitamins, xanthines, anti-neoplastic agents, proteins, polypeptides, carbohydrates, polynucleotides, nucleic acids, and polyclonal or monoclonal antibodies.

EXAMPLES

For a better understanding of the invention, provided hereinafter are examples of embodiment having an explanatory and non-limiting purpose.

In the ensuing examples, the size of the nanohydrogel particles were measured with the DLS (Dynamic Light Scattering) technique (Submicron Particle Sizer Autodilute Model 370, Nicomp).

Example 1: Sterilization and Homogenization of Gellan Gum-Cholesterol (Ge-CH) Nanohydrogels A dispersion in water of Ge-CH nanohydrogels at concentration of 1 mg/ml was obtained. An amount of 3 ml of this dispersion was introduced into a glass container, which was then closed and put into an autoclave for sterilization and homogenization. In the autoclave the dispersion was subjected for 20 minutes to a temperature of 121° C. and a pressure of 2 bar. Said treatment rendered the nanohydrogels sterile and apyrogenic according to the requirements of European pharmacopoeia. Furthermore, the autoclave treatment obtained a homogenization of the specimen and induced a reduction of the particle size, which, from an initial diameter of 170±10 nm prior to treatment, reached after treatment a mean diameter of 120±8 nm, and a reduction of the polydispersion index, which from a value of 0.350±0.050, passed to a value of 0.200±0.030 after treatment.

The dimensional stability of the Ge-CH nanohydrogels was studied at 37° C. for 15 days so as to mimic the physiological conditions, and at 4° C. for 15 days so as to mimic the conditions of preservation of the product in a refrigerator. The Ge-CH nanohydrogels treated with the method according to the present invention proved stable at high and low preservation temperatures.

Furthermore, the potential $\zeta$ of the Ge-CH nanohydrogels was measured using the DLS (Dynamic Light Scattering) technique, and the value obtained was −20±5.0 mV and remained stable for over 48 hours.

Example 2: Sterilization and Homogenization of Hyaluronic Acid-Cholesterol (HA-CH) Nanohydrogels A dispersion in water of HA-CH nanohydrogels at a concentration of 1.5 mg/ml was obtained. An amount of 3 ml of this dispersion was introduced into a glass container, which, once closed, was put into an autoclave. In the autoclave, the dispersion was subjected for 45 minutes to a temperature of 105° C. and a pressure of 1.5 bar.

Said method rendered the nanohydrogels sterile and apyrogenic according to the requirements of the European pharmacopoeia. Furthermore, the particle size was measured, and it was noted that the treatment obtained a homogenization of the specimen. In particular, there was found a reduction of the particle size, which, from an initial diameter of 200±10 nm prior to treatment, reached a mean diameter, after treatment, of 150±10 nm and a reduction of the polydispersion index, which, from a value of 0.40±0.05 passed to a value of 0.30±0.05 after the treatment. It was found that the sterile HA-CH nanohydrogels showed a dimensional stability in time for over 30 days at 4° C. and for over 7 days at 37° C.

Example 3: Sterilization, Homogenization, and Charging with Cryoprotectant of Hyaluronic Acid-Cholesterol (HA-CH) Nanohydrogels A dispersion in water of HA-CH nanohydrogels at a concentration of 1.5 mg/ml was obtained. An amount of 3 ml of this dispersion was added with dextrose as cryoprotectant until a concentration of 1% w/v was obtained, and was introduced into a glass container. The container was closed and put into an autoclave. In the autoclave, the dispersion was subjected for 60 minutes to a temperature of 100° C. and a pressure of 1.5 bar.

At the end of the treatment, HA-CH nanohydrogels charged with the cryoprotectant dextrose and having a size of 380±20 nm measured using the method reported for the foregoing examples were obtained.

The nanohydrogels thus obtained were subjected directly to lyophilization according to the known techniques so as to obtain a lyophilizate that is convenient to transport and handle and stable over long periods of time. Subsequently, the lyophilizate obtained was re-dispersed with sterile water, and it was possible to re-obtain the HA-CH nanohydrogels with a size of 400.0±10.0.

Example 4: Sterilization, Homogenization, and Charging with Levofloxacin of Gellan Gum-Cholesterol (Ge-CH) Nanohydrogels An aqueous solution of the drug (levofloxacin, 0.33 mg/ml) was added to a dispersion of Ge-CH nanohydrogels (1.0 mg/ml) (1:3 w/w drug/polymer). An amount of 3 ml of the dispersion thus obtained was introduced into a glass container, which, once closed, was put into an autoclave. In the autoclave, the dispersion was subjected for 20 minutes to a temperature of 130° C. and a pressure of 2.5 bar. At the end of the process, the dispersion was subjected to dialysis (Visking tubing, cut-off: 12000-14000) for 3 hours against distilled water so as to purify the nanohydrogels from the drug not encapsulated therein. Before the treatment in the autoclave, the Ge-CH nanohydrogels had a size of 266±3 nm with a polydispersion index of 0.30±0.03, whereas after treatment, Ge-CH nanohydrogels charged with levofloxacin with a size of 240±5 nm and a polydispersion index of 0.30±0.01 were obtained.

In order to evaluate the trapping efficacy of the drug in the Ge-CH nanohydrogels, these were lyophilised and solubilized in N-methyl-pyrrolidone so as to break the nanohydrogels and free the levofloxacin trapped therein. The trapping efficacy (percent encapsulation) was determined by the ratio of the amount of levofloxacin encapsulated in the nanohydrogels to the total amount of nanohydrogels produced. The concentration of levofloxacin in solution was measured using a UV-VIS spectrophotometer at the absorbance wavelength of levofloxacin (302 nm), using a calibration straight line that was obtained in a concentration range of between 0.75 µg/ml and 12.0 µg/ml. The trapping efficacy of levofloxacin in the Ge-CH nanohydrogels, charged at high pressure and high temperature, was 3% with respect to the weight of the polymer.

The dispersion of charged nanohydrogels was then lyophilised according to the classic methodology, adding thereto a solution of cryoprotectant (dextrose) at a final concentration of 1% w/v. The lyophilizate was then re-suspended so as to reconstitute then nanohydrogels with the drug trapped therein.

Example 5: Sterilization, Homogenization, and Charging with Levofloxacin and Cryoprotectant of Hyaluronic Acid-Cholesterol (HA-CH) Nanohydrogels An amount of 9 mg of HA-CH nanohydrogel particles was dispersed in 3 ml of an aqueous solution comprising dextrose as cryoprotectant at the concentration of 1% w/v. The dispersion formed was added with 1 ml of a solution of a fluoroquinolone antibiotic (levofloxacin) to obtain a final concentration of antibiotic of 1 mg/ml. The mixture thus obtained was introduced into an appropriate glass container, which, once closed, was put into an autoclave. In the autoclave, the dispersion was subjected for 30 minutes to a temperature of 110° C. and a pressure of 2 bar.

At the end of the process, the dispersion was subjected to sterile diafiltration so as to purify the nanohydrogels from the drug not encapsulated therein. After filtration, there were obtained HA-CH nanohydrogels charged with levofloxacin and sterile, having a size of 380±20 nm, and with a polydispersion index of 0.325±0.07.

The nanohydrogels produced were lyophilised according to the known techniques, and then the lyophilizate was re-dispersed in an amount of sterile water such as to obtain a concentration of charged nanohydrogels equal to 1 mg/ml. The dispersion was sized with the DLS technique, and from the results it emerged that, in these conditions, the nanohydrogels maintain roughly the same starting size (384±7 nm).

In order to evaluate the trapping efficacy of the drug in the HA-CH nanohydrogels, these were lyophilised and solubilized in N-methyl-pyrrolidone so as to break the nanohydrogels and free the levofloxacin trapped therein. The trapping efficacy (percent encapsulation) was determined by the ratio of the amount of levofloxacin encapsulated in the nanohydrogels to the amount of nanohydrogels. The concentration of levofloxacin in the dispersion was measured using a UV-VIS spectrophotometer at the wavelength of absorbance of levofloxacin of 302 nm and using a calibration straight line that was obtained in a concentration range of between 0.75 µg/ml and 12.0 µg/ml.

The trapping efficacy of levofloxacin in HA-CH nanohydrogels was 5% with respect to the weight of the polymer.

From the description of the examples referred to above it is evident how the treatment method according to the present invention presents the major advantage both of sterilizing the nanohydrogels in an extremely simple and economically advantageous way and to provide nanohydrogels charged with compounds that are able to bestow upon the nanohydrogels themselves important applicational developments.

Furthermore, the treatment forming the subject of the present invention increases the dimensional homogeneity of the nanohydrogels.

With the treatment forming the subject of the present invention, the nanohydrogels can encapsulate or adsorb a large number of active principles, which are protected by the polymeric system during the process of sterilization and homogenization.

It should be pointed out how the treatment method forming the subject of the present invention enables preparation of sterile and apyrogenic nanohydrogels charged with a pharmacologically active principle without causing degradation of the latter or degradation of the polymer.

The treatment forming the subject of the present invention presents the major advantage of rendering the nanohydrogels sterile and apyrogenic and of charging them both with a drug and with a cryoprotective compound. This involves that the sterile and apyrogenic nanohydrogels vehicling the drug can be subjected to a lyophilization process so as to be preserved in the form of lyophilizate that is stable over long periods and convenient to handle and transport. Lyophilized nanohydrogels can be reconstituted in water or in adequate solutions, such as for example physiological solutions, perserving the same initial characteristics.

Finally, it should be emphasized how the treatment method according to the present invention is not aimed exclusively at applications of a biomedical and/or pharmaceutical nature, but can be employed effectively in all those applications that require the use of polysaccharidic nanohydrogels.

The invention claimed is:

1. A method for treating nanohydrogels, characterized in that it comprises a dispersion step, in which a nanohydrogel obtained from a polysaccharide functionalized with hydrophobic molecules is dispersed in an aqueous solution to obtain an aqueous dispersion of nanohydrogels, and a sterilization and homogenization step, in which said aqueous dispersion of nanohydrogels is subjected to a temperature of between 70° C. and 150° C. and a pressure of between 1 and 5 bar; in said sterilization and homogenization step the conditions of temperature and pressure must be such that boiling of the aqueous dispersion of nanohydrogels does not occur.

2. The method for treating nanohydrogels according to claim 1, characterized in that the sterilization and homogenization step envisages a temperature of between 90° C. and 130° C. and a pressure of between 1.5 bar and 3.5 bar.

3. The method for treating nanohydrogels according to claim 1, characterized in that the sterilization and homogenization step has a duration of between 5 min and 3 h.

4. The method for treating nanohydrogels according to claim 1, characterized in that the sterilization and homogenization step envisages that added to the aqueous dispersion of nanohydrogels is a compound designed to be charged in the nanohydrogels particles by being englobed or adsorbed thereby.

5. The method for treating nanohydrogels according to claim 4, characterized in that the aforesaid compound designed to be englobed and/or adsorbed in the nanohydrogel particles is a cryoprotective compound and/or a pharmacologically active compound.

6. The method for treating nanohydrogels according to claim 5, characterized in that said cryoprotective compound is added to the aqueous dispersion of nanohydrogels in a concentration of between 0.10-20.0% w/v.

7. The method for treating nanohydrogels according to claim 5, characterized in that said pharmacologically active compound is added to the aqueous dispersion of nanohydrogels in a concentration of between 0.05 mg/ml and 10.0 mg/ml.

* * * * *